United States Patent [19]

Bronstert et al.

[11] Patent Number: 4,861,742
[45] Date of Patent: Aug. 29, 1989

[54] BIFUNCTIONAL ALKALI METAL COMPOUNDS, PREPARATION AND USE THEREOF AS POLYMERIZATION INITIATORS

[75] Inventors: Klaus Bronstert, Carlsberg; Siegbert Bohnet, Mannheim; Walter Himmele, Walldorf; Kaspar Bott, Mannheim, all of Fed. Rep. of Germany

[73] Assignee: BASF Aktiengesellschaft, Ludwigshafen, Fed. Rep. of Germany

[21] Appl. No.: 238,851

[22] Filed: Sep. 1, 1988

[30] Foreign Application Priority Data

Sep. 1, 1987 [DE] Fed. Rep. of Germany ....... 3729144

[51] Int. Cl.$^4$ ............................ C08F 4/46; C08F 4/48
[52] U.S. Cl. ................................ 502/157; 260/665 R; 546/152; 546/255
[58] Field of Search ............... 502/157, 546, 152, 255; 260/665 R

[56] References Cited

U.S. PATENT DOCUMENTS

| | | | |
|---|---|---|---|
| 3,251,812 | 5/1966 | Hsieh | 260/79.5 |
| 3,644,322 | 2/1972 | Farrar | 502/157 X |
| 3,663,634 | 5/1972 | Morton et al. | 502/157 X |
| 3,933,774 | 1/1976 | Neumayr et al. | 502/157 X |
| 4,067,917 | 1/1978 | Sigwalt et al. | 260/665 R |

FOREIGN PATENT DOCUMENTS

| | | |
|---|---|---|
| 2623344 | 12/1976 | Fed. Rep. of Germany . |
| 135619 | 3/1975 | German Democratic Rep. . |
| 55-50003 | 4/1980 | Japan ............... 502/157 |
| 2083041 | 3/1982 | United Kingdom ........ 502/157 |

*Primary Examiner*—Patrick P. Garvin
*Attorney, Agent, or Firm*—Oblon, Spivak, McClelland, Maier & Neustadt

[57] ABSTRACT

Bifunctional initiators for anionic polymerization are prepared by reacting an alkenylaromatic compound of the general formula I

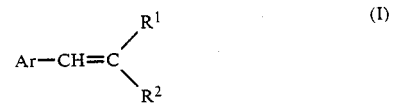

where Ar is aromatic hydrocarbyl which may be substituted by alkyl or another group inert toward organoalkali metal compounds and may contain nitrogen, R$^1$ is linear or branched alkyl, cycloalkyl, alkenyl or aralkyl or from 1 to 22 carbon atoms where at least the carbon adjacent to the double bond is saturated and aliphatic, R$^2$ is hydrogen or is likewise linear or branched alkyl, cycloalkyl, alkenyl or aralkyl or from 1 to 22 carbon atoms where at least the carbon adjacent to the double bond is saturated and aliphatic, and where R$^1$ and R$^2$ may be part of a common cycloaliphatic ring, in the presence of one or more ethers and of tertiary amines and in the presence or absence of a further inert aliphatic, alicyclic or aromatic solvent, at from −20° to +70° C. with preferably lithium and with dimerization, with the use in addition of poly-cyclic aromatic hydrocarbons which catalytically promote the dimerization in amount of from 0.001 to 50, preferably 20, mol % and with or without the removal of the ethers and/or tertiary amines after the preparation, and are used for polymerizing anionically polymerizable monomers such as styrene.

6 Claims, No Drawings

BIFUNCTIONAL ALKALI METAL COMPOUNDS, PREPARATION AND USE THEREOF AS POLYMERIZATION INITIATORS

The present invention concerns novel bifunctional organoalkali metal compounds, in particular those of lithium, a process for preparing same and the use thereof as initiators for anionic polymerization.

It is known to use organoalkali metal compounds as catalysts for the anionic polymerization of, preferably, alkenylaromatics and/or dienes. Particularly highly suitable instances are lithium alkyls, since they are comparatively stable and, unlike the corresponding sodium or potassium alkyls, are also soluble in hydrocarbons and make possible polymerizations therein. Living polymers having lithium end groups, furthermore, are convertible with suitable reagents in particularly high yields into terminally functionalized polymers, for example into those having —OH, —SH or amino groups. These reactions perform best when the reaction medium for the most part comprises hydrocarbon.

While existing monofunctional lithium alkys meet all the requirements for the use as catalysts for anionic polymerization, existing bifunctional initiators have defects. Such catalysts are required in particular if polymers functionalized at both ends of the chain are to be produced.

For instance, the reaction product of stilbene (cf. U.S. Pat. No. 3,251,812) or 1,1-diphenylethylene and lithium (cf. U.S. Pat. No. 3,663,634) can only be prepared and used in polar solvents such as ethers or tertiary amines because they are insoluble and unstable in hydrocarbons. They are frequently not sufficiently active and/or lose some of their activity in the initial step of polymerization, so that in part or predominantly they give monofunctionally grown polymers and/or polymers having a wide molecular weight distribution.

It is further known to prepare multifunctional organometallic initiators for the anionic polymerization of vinyl compounds or dienes by reacting lithium alkyls with diethylenically unsaturated aromatic compounds, for example divinylbenzene or diisopropenylbenzene. Such initiators are described in GB Pat. No. 2,111,057. They are prepared in the presence of several times the molar amount of tertiary amines. Nevertheless, their stability is unsatisfactory, and in the preparation of polymers the formation of insoluble crosslinked portions is difficult to prevent.

Plaste und Kautschuk 26 (1979), 263–64, describes in a similar form the preparation of an initiator based on divinylbenzene and having a functionality of 2.4, again in the presence of a tertiary amine. If such multifunctional initiators prepared in the presence of polar compounds or solvents are used to polymerize dienes, the structure of the polymerization products is changed in that the monomers are predominantly incorporated in the 1,2- or 3,4-position and not as desired for many purposes predominantly in the 1,4-cis or 1,4-trans configuration. These catalysts are likewise not stable in hydrocarbons.

Although there are publications (for example C.A.H. Acad. Sci., Ser. C. 283 (1976), 123–25) according to which the presence of a polar compound is not necessary, an attempt to repeat the work showed that such initiators lead predominantly to the formation of monofunctionally grown polymers. For instance, polymers prepared by means of such catalysts by successive polymerization of butadiene and styrene do not have the properties of elastomers, as would be typical of the expected 3-block copolymers, but a plasticity characteristic of 2-block copolymers.

It is an object of the present invention to provide bifunctional alkali metal initiators, preferably of lithium, which are soluble and stable even in media comprising predominantly hydrocarbons and which do not contain any monofunctional portions. It is a further object to provide a process suitable for preparing such dialkali metal compounds and the use thereof for the preparation of living polymers grown at both ends of the chain and the functionalization thereof.

We have found that these objects are achieved with a process for preparing a bifunctional initiator for polymerizing an anionically polymerizable monomer, which comprises dimerizing an alkenylaromatic compound of the general formula I

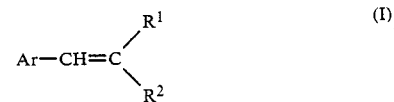

at from −20° to +70° C. with an alkali metal under an inert gas atmosphere.

In the formula I,

Ar is an aromatic, even polycyclic, ring system which may contain nitrogen and may be substituted by groups which do not react with organoalkali metal compounds. Ar can be for example phenyl, alkylphenyl, m-methoxyphenyl, naphthyl, alkylnaphthyl, biphenyl, phenoxyphenyl, pyridyl or quinolyl. Preferably, A is phenyl.

$R^1$ is linear or branched alkyl, alkenyl, aralkyl or cycloalkyl of preferably from 1 to 22 carbon atoms which may also contain oxoether or thioether bridges, provided they do not react with lithium alkyls, or is aralkyl where, however, at least the carbon atom adjacent to the double bond must be aliphatic. $R^1$ may also link to Ar in the form of an annular bridge which, however, aside from the double bond must have no fewer than 2 aliphatic carbon atoms.

$R^2$ is hydrogen or linear or branched alkyl, cycloalkyl, alkenyl or aralkyl of preferably from 1 to 22 carbon atoms which may also contain oxoether or thioether bridges, provided they do not react with lithium alkyls, or is a specific aralkyl radical where at least the carbon atom adjacent to the double bond is aliphatic.

$R^1$ and $R^2$ may also contain more than 22 carbon atoms.

$R^1$ and $R^2$ may together form an alicyclic ring.

Preferably, Ar is phenyl or naphthyl, $R^1$ is linear or branched alkyl of from 1 to 10 carbon atoms or cycloalkyl of 5–8 carbon atoms and $R^2$ is hydrogen.

Particularly suitable β-substituted alkenylaromatics for the purposes of the present invention are for example β-alkylstyrenes, such as β-methylstyrene, β-ethylstyrene, β-butylstyrene, β-ethylhexylstyrene, m-methoxy-β-methylstyrene, 1,3-diphenyl-1-propene and the like. Preference is further given to compounds where Ar is phenyl, $R^1$ and $R^2$ are each linear or branched alkyl of from 1 to 8 carbon atoms or constituents of a cycloaliphatic ring of from 5 to 12 carbon atoms and the alkali metal is lithium. To obtain a high yield the dimerization then preferably takes place in the presence of small amounts of catalytically active polycyclic hydrocarbons.

A suitable β,β-dialkylstyrene is for example β,β-dimethylstyrene. This list is not complete and is not intended to limit the number of possible starting materials.

The exothermic dimerization of vinylaromatics is effected by reaction in the presence of one or more ethers and one or more tertiary amines and in the presence or absence of inert aliphatic, alicyclic and/or aromatic solvents at from −20° to +70° C., preferably at from 0° to 40° C., with an alkali metal. Concentrations of more than 100 millimoles per liter necessitate efficient temperature regulation. If inert hydrocarbons are used the amount of ethers and/or tertiary amines present in the reaction medium should be greater than 2 moles per mole of β-alkyl-vinylaromatic in order to ensure an adequate rate of reaction and comolete conversion.

Particularly highly suitable ethers are aliphatic ethers, for example dimethyl ether, diethyl ether, dipropyl ether, dibutyl ether, diisopropyl ether, t-butyl methyl ether and the like, and also tetrahydrofuran and other alicyclic ethers. The reaction proceeds rapidly in their presence at room temperature and frequently ends as early as from 15 to 60 minutes with more than 80% by weight, preferably more than 95% by weight, of the β-alkylvinylaromatic being dimerized. If, by contrast, less suitable aromatic ethers are used, such as anisole or phenetole, the reaction takes 10 times as long without going to completion. Owing to undesirable secondary reactions the lithium content in the reaction medium is then appreciably above the level of (lithium-based) polymerization activity.

Suitable tertiary amines are not only trialkylamines, such as triethylamine, trimethylamine and the like, but also alicyclic or aliphatic/aromatic amines such as N-methylcyclohexylamine or dimethylaniline.

Besides ethers it is possible with some starting materials, in particular the less reactive β,β-dialkylstyrenes or the overly active β-methylvinylaromatics, to improve the yield of target product by the addition of polycyclic aromatic hydrocarbons which catalyze the dimerization in amounts of from 0.001–50, preferably 1–20, mol %, based on the starting material. Examples of polycyclic aromatic hydrocarbons are phenanthrene, anthracene, naphthalene, biphenyl and m- or p-terphenyl. The alkali metal used is preferably lithium, but sodium or potassium also give useful catalysts.

The reaction benefits from mechanical mixing, since lithium, owing to its low density, floats on the surface of the liquid reaction medium. If sodium-containing catalysts are to be prepared, it is useful to use the liquid Na-K alloy in a molar ratio of 1:1, from which, if present in excess, only the sodium is used up in the course of the reaction.

After the dimerization, volatile ethers may be distilled off under atmospheric or reduced pressure, during which the temperature should not exceed 35° C., preferably 25° C. Besides the ethers there are advantageously also present hydrocarbons having higher boiling points than the ethers. The solubility of the catalysts according to the invention is usually retained if tetrahydrofuran is used, provided not less than 2 moles of ether are present per mole of polymerization-active alkali. If all the ether is distilled off, such catalysts, which are prepared from β-alkylstyrenes having short linear alkyl groups, become sparingly soluble and precipitate in part or as a whole as usually pale orange crystals. Catalysts based on β-methylstyrene are least soluble. If such suspensions are used for the polymerization, the solids go into solution after some time. However, wider molecular weight distributions are produced. But catalysts based on β-alkylstyrenes having long or/and branched alkyl groups remain in solution. They do not have these disadvantages.

If the catalyst has been prepared in the presence of tetrahydrofuran, in the distillation it is normally only possible to reduce the ether content to 1 mole per mole of polymerization-active lithium, because tetrahydrofuran forms a very stable complex with the catalyst. If, by contrast, the preparation was carried out using low-boiling aliphatic ethers, for example dimethyl ether, diethyl ether, diisopropyl ether or t-butyl methyl ether, or low molecular weight tertiary amines, for example triethylamine, they are easily reducible to residual levels of less than 0.2 mole per mole of polymerization-active lithium. To ensure that these catalysts retain their solubility in hydrocarbons, the starting materials need to be β-alkylstyrenes where the alkyl contains no fewer than 4, preferably 6, carbon atoms. The best configuration also depends on the radical Ar and must be determined from case to case.

Catalysts which contain no or little alicyclic or aliphatic ether and those which contain only aromatic ethers, such as anisole or phenetole, incorporate dienes predominantly in the 1,4-configuration on polymerization. Such polymers are known to be less heat-sensitive or prone to crosslinking and have better mechanical properties than polymers which contain dienes in the 1,2-or 3,4-configuration.

If catalysts containing less than 2 moles of aliphatic or cycloaliphatic ether are used, however, the polymers produced frequently have higher molecular weights than arithmetically expected from the monomer/catalyst ratio. It is therefore preferable to use catalysts containing activity.

If catalysts prepared in the presence of tertiary amines are used, the dienes incorporated in the polymer have even for high ratios of amine:polymerization activity, for example from 5 to 15, only a slightly higher level of 1,2-configuration.

All solvents and the β-substituted vinylaromatics need to be thoroughly freed of contamination before use. A suitable method is for example the distillation over a metal alkyl such as aluminum triethyl. The reactions should be carried out under an inert gas atmosphere, for example dry, oxygen-free nitrogen or argon.

Solutions of the dialkali metal or dilithium catalysts are intensely colored. The color varies with the starting material from orange to dull bluish red to bluish black. Each mole of alkenylaromatic used gives rise to up to one mole of polymerization-active groups. This content, hereinafter referred to as PA, can be determined by titration of an aliquot of the solution under inert conditions with i-propyl alcohol until the color changes to colorless. The PA content in general shows good conformity with the alkali metal content of the solution. The preparation of the catalyst is virtually free of any lithium-consuming secondary reaction.

The reaction according to the invention theoretically leads to 1,4-dilithium-1,4-diaryl-2,3-dialkylbutane or 1,4-dilithium-1,4-diaryl-2,2,3,3-tetraalkylbutane

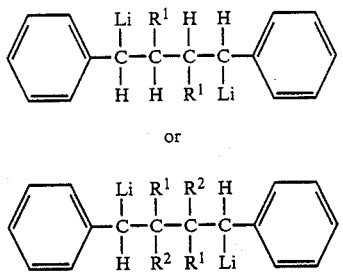

or or the corresponding other alkali metal compounds.

We have found, then, that the reaction comes closest to the theoretical ideal on using alkenylaromatics where $R^1$ is an aliphatic radical of no fewer than 2 carbon atoms and $R^2$ is hydrogen. Dilithium compounds of the formula I are then formed in almost theoretical yield. It is immaterial which of the structural isomers β-cisalkyl-vinylaromatic or β-trans-alkylvinylaromatic is used as the starting material.

If a β-methylvinylaromatic, for example β-methylstryene, is used, the products in addition to the dimers also include oligomers, preferably trimeric or tetrameric dilithium compounds having presumably for example the following structure (for the tetramer):

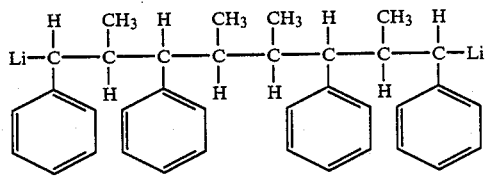

Although these tetramers are likewise stable bifunctional initiators, the formation of oligomers is preventable by carrying out the reaction in the presence of catalytic amounts, for example from 0.1 to 10 mol %, of polycyclic aromatics. Suitable aromatics are for example phenanthrene, naphthalene, anthracene, biphenyl, the various isomeric terphenyls, etc. They serve to increase the yield of polymerization activity, based on starting β-methylstyrene.

If the starting material used is a β,β-dialkyl-vinylaromatic, its low activity frequently results in incomplete conversion. However, if the reaction is carried out in the presence of the above-described polycyclic aromatic compound the dilithium compound of the formula II forms in almost quantitative yield under optimal conditions. The catalysts according to the invention have high stability. There is no observable decrease in polymerization activity even after 100 days' storage at room temperature.

The lithium-based catalysts according to the invention differ in hydrocarbon solubility depending on composition. The soluble species are capable of polymerizing diolefins or alkenylaromatics in the presence of small amounts of ether, for example from 1 to 5 moles per mole of polymerization activity, to polymers of narrow molecular weight distribution just as well as monofunctional lithium catalysts. The functionalization of the resulting living polymers is possible in high yields.

The corresponding sodium catalysts are only sparingly soluble in hydrocarbons. Nevertheless, they too are capable of catalyzing the polymerization of for example styrene in cyclohexane or other hydrocarbons, in the course of which they dissolve, giving wider molecular weight distributions than lithium catalysts. In the presence of small amounts of ether, for example from 5 to 10 moles per mole of polymerization activity, however, the catalysts are soluble with proper selection of suitable starting materials and produce narrow molecular weight distributions. The polymerization of dienes is more difficult.

The novel dilithium compounds in particular are excellent bifunctional initiators for the anionic polymerization of for example alkenylaromatics and/or dienes. In general they contain no monofunctional portions. They produce polymers having a narrow molecular weight distribution, so that the molecular weights determined from the catalyst:monomer ratio are in relatively good agreement with the values determined by gel permeation chromatography.

The catalysts according to the invention give bifunctionally growing polymers. If first butadiene and then styrene are polymerized in succession, this gives in 2 stages 3-block copolymers which in terms of properties correspond to those polymers of the same composition which are prepared y existing methods in a 3-stage polymerization styrene→butadiene→styrene using a monofunctional catalyst. Following oxidative degradation of the butadiene portion of the polymer with osmium tetroxide (cf. Angw. Makromol. Chem. 26 (1972), 207) the remaining polystyrene blocks have the same molecular weight in both cases.

The viscosity of active polymer solutions prepared with the initiators according to the invention is much higher for the same molecular weight than that of polymers prepared using monofunctional catalysts, since the two ionic chain ends form a reversible network by association. The lower the level of ether in the solvent mixture, the higher the degree of association. Furthermore, association is enhanced to such an extent by conversion of the carbanion end groups with terminating reagents into for example lithium amide, lithium alcoholate or lithium thiolate end groups that even at low polymer concentrations and molecular weights gelling results in the formation of an aspiclike mass. Intensive stirring at high torque is necessary to mix through the mass to obtain complete conversion. If this gel is admixed with water or an active hydrogen compound, the ionic cross-linking is eliminated and the solution becomes as fluent as water.

The functionalization of living chain ends is known. Suitable functionalizing reagents are for example oxiranes, which provide terminal primary or secondary hydroxyl functions (cf. U.S. Pat. No. 3,786,116), and thiiranes, whereby terminal thiol groups can be introduced. According to EP-A No. 0,211,395 or European Patent Application No. 87 103 893.1, it is possible to obtain polymers which have at the end of the chain at least one amino group. The reactions are described in detail in said specifications, so that no description is necessary here, although it can in part be read from the Examples below. These polymers, if wholly or partly built up from dienes, may further be hydrogenated, causing all or some of the aliphatic double bonds to disappear. The hydrogenation is carried out by means of molecular hydrogen and catalysts based on metals or metal salts of group VIII of the periodic table, either in homogeneous or heterogeneous phase. The processes are known and are described for example in U.S. Pat.

No. 3,113,986, DE-B No. 1,222,266, DE-A No. 2,013,263, DE-B No. 1,106,961 or DE-A No. 1,595,345.

Functionalized polymers which have been prepared according to the invention from dienes or vinylaromatics and which contain amino or hydroxyl groups at the chain ends can be crosslinked for example with diisocyanates and other reagents. Solutions of such polybutadienes, admixed with diisocyanates, cast onto siliconized paper and dried, produce elastic, dry, hydrocarbon-insoluble films which can be peeled off the substrate and show high reversible extensibility.

Polymers functionalized at both chain ends with mercapto, hydroxyl or amino groups are of particular interest for use as prepolymers for polyurethanes, epoxy and other resins and for the modifying thereof. The preparation of epoxy resins and elastomeric polyurethanes consisting of a rigid segment comprising aromatic polyisocyanates and a flexible segment comprising functionalized flexible macromolecules is known and is described by H. P. Elias in Makromoleküle, pages 778–780 and 802–812, 4th Edition (1981), H tuig und Wepf Verlag Basle-Heidelberg-N.Y. and the references cited therein.

Polybutadienediols as flexible segments in thermoplastic polyurethanes are notable for particularly good segregation of rigid and flexible segments, which is desirable for application and processing reasons, as indeed described by Becker and Braun, Kunststoffhandbuch Volume 7, Polyurethanes, page 33 (1983), 2nd Edition Hanser Verlag, Munich-Vienna. For the same weight average molecular weight such oils, having a narrow molecular weight distribution from preparation according to the invention, have a much lower viscosity than known prepolymers such as telechelic polybutadiene oils, polytetrahydrofuran or polyesters prepared by free radical polymerization. They are therefore much more easily processible.

Polymers obtained according to the invention have in general a weight average molecular weight Mw of from 5,000 to 500,000, preferably of from 3,000 to 130,000, determined by gel permeation chromatography (GPC) and compared with standardized polymers suitable for calibrating purposes (cf. G. Glöckner, Polymercharakterisierung durch Flussüigkeitschromatographie, Verlag A. Hüthig, Heidelberg, 1982). The measurement is carried out at 23° C. in 0.25% strength by weight tetrahydrofuran solution at a flow rate of 1.2 ml/min. The molecular weight is expediently determined prior to the functionalization, since some functionalized polymers are adsorbed on GPC columns, rendering the latter inoperable.

The polymers are worked up in a conventional manner, for example by precipitation with nonsolvents, by evaporating off the solvent or by steam distillation. Even devolatilization on devolatilization extruders is, possible.

The Examples below illustrate the invention without limiting it.

Starting materials:

The β-substituted vinylaromatics were prepared by a conventional method of organic chemistry. To prepare β-monoalkylstyrenes, for example phenylmagnesium bromide was reacted with aldehydes and the resulting alkylbenzyl alcohols were dehydrated. To prepare β,β-dialkylstyrenes, sec-bromomagnesium alkyls were reacted with benzaldehyde and the resulting 1-phenyl-2,2-dialkylethanols were likewise dehydrated. The end products were purified by distillation via a multiplate column using a high reflux ratio. This preferably gives the higher-boiling transisomers in high purity, while the cis-isomers, which are formed in minor amounts, are present in the first cut.

The following alkenylaromatics were used:

| Alkenylaromatic | Structure | bp. mm | Content in area % by gas chromatography |
| --- | --- | --- | --- |
| A Trans-β-methylstyrene | | 117–119/120 | 99.9 |
| B Trans-β-ethylstyrene | | 84/22 | 99.9 |
| C Trans-β-butylstyrene | | 130/36 | 99.8 |
| D Trans-β-isopropylstyrene | | 88/16 | 99.8 |
| E Trans-β-hexylstyrene | | 110–112/6 | 99.9 |

-continued

| | Alkenylaromatic | Structure | bp. mm | Content in area % by gas chromatography |
|---|---|---|---|---|
| F | Cis-β-hexylstyrene | | 156/22 | 99.4 |
| G | Trans-1-vinyl-β-methyl-naphthalene | | 88/2 | 96.2 of trans + 3.8 of cis |
| H | Trans-1,3-diphenyl-1-propene | | 111–112/2 | 99.6 |
| J | Trans-1,4-diphenyl-4,4-di-methyl-1-butene | | 129–131/2 | 99.2 |
| K | Trans-β-pentylstyrene | | 75/2 | 99.9 |
| L | Trans-β-nonylstyrene | | 104/2 | 99.6 |
| M | Trans-1-phenyl-5-methyl-7,7-dimethyl-1-octene | | 167–168/18 | 99.4 |
| N | Trans-1-phenyl-3-methyl-5,5-di methyl-1-hexene | | 77/2 | 99.3 |
| O | Trans-1-phenyl-3-ethyl-1-octene | | 162/2 | 99.7 |
| P | β,β-Dimethylstyrene | | 98/64 | 99.9 |

The solvents (benzene, t-butylbenzene, methylcyclohexane, octane, tetrahydrofuran, diethyl ether, dibutyl ether, diisopropyl ether, triethylamine, anisole) were freed of impurities by addition of sufficient secbutyllithium and a small amount of styrene as indicator as to leave a persistent orange color, and distilled off under pure nitrogen. Storage was likewise under pure nitrogen.

The dimthethyl ether, which boils at −25° C., was taken from a pressure flask, purified in a washing flask charged with sec-butyllithium/methylcyclohexane solution and introduced into the reactor in gas form.

The commercially available pure nitrogen was washed in 2 washing flasks connected in series with a mixture of white oil, 1% by weight of styrene and 5% by weight of lithium butyl.

Lithium was used in the form of granules from 1 to 5 mm in size available inter alia from Merck-Schuchhardt.

Sodium was used in the form of an alloy with potassium in a molar ratio of 1:1.

The polymerization runs were carried out with commercial butadiene and styrene. Before use the monomers were purified by distilling off 0.5% by weight of triisobutylaluminum.

Functionalization was effected with 1,5-diazabicyclo[3.1.0]hexane, described in European Patent Application No. 87 103 893.1 and hereinafter referred to as propylenediaziridine.

Analytical (a) Characterization of catalysts according to the invention (aa) Determination of polymerization activity (PA)

In what follows, PA is the level of polymerization-active lithium. 1 mole of difunctional catalyst thus corresponds to 2 moles of PA.

A calibrated 5 cm$^3$ disposable syringe made of polypropylene (from Braun-Melsungen AG, West Germany) and having a 15 cm long needle is used to sample the reactor or stock reservoir vessel under inert conditions (the syringe is freed of impurities by repeatedly syphoning up and discharging reactor contents) to remove an amount of solution containing about 2–3 millimoles of polymerization activity and to discharge this sample through a rubber cap into a 500 cm$^3$ flask flushed with pure nitrogen and containing 100 cm$^3$ of previously introduced toluene stirred with a magnetic stirrer. Impurities in the toluene have previously been titrated away with the reaction solution to a slight yellow color. The intensely colored solution is then titrated with 1N isopropanol in absolute toluene from a 5 cm$^3$ capacity calibrated injection syringe until the color disappears. The total amount of polymerization activity PA in the reactor is then calculated from $$\frac{\Sigma \text{ stock reservoir } + \text{ sample (cm}^3)}{\text{cm}^3 \text{ of sample}} \times$$

cm$^3$ of 1 N i-propyl = millimoles of PA (ab) Determination of alkali content

As described under aa, an amount of catalyst solution corresponding to about 1 millimole of PA is removed and added under nitrogen to a mixture of 10 cm$^3$ of cyclohexane and 1 cm$^3$ of methanol. The colorless mixture is then shaken with 20 cm$^3$ of distilled water. After the phases have separated the clear aqueous extract is removed with an injection syringe and the solution is extracted a further 2 times with 10 cm$^3$ of water each time. The combined extracts are evaporated in an Erlenmeyer flask until the organic solvents have been removed. After the contents have been cooled down, they are tritrated with N/10 HCl and phenolphthalein until neutral.

$$\frac{\Sigma \text{ stock reservoir } + \text{ sample (cm}^3)}{\text{cm}^3 \text{ of sample} \times 10} \times$$

cm$^3$ of N/10 HCl = millimoles of alkali (ac) Determination of oligomer content of catalyst by GPC analysis The organic extract from ab) is evaporated to dryness at 50° C. in a waterbath under a stream of nitrogen, and the last traces of water are then removed at room temperature under reduced pressure. The residue is weighed and made into a 0.1% strength by weight solution with tetrahydrofuran.

Separation is effected by high pressure liquid chromatography (HPLC) with tetrahydrofuran over a ®Lichrogel column PS4 from Merck, Darmstadt, at a flow rate of 1.0 cm$^2$/min. The combination L5000 LC-Controler and pump 655H-11 from Merck, Darmstadt, was used.

The peaks for starting material, dimer and oligomer are identified by reference to a calibration curve obtained with oligomers of styrene. The component fractions are determined from the area percentages from the refractive index detector (from ERC, type 7510). In addition, the separation is monitored in the UV which, owing to the high molar absorbance, is particularly highly suitable for detecting unconverted $\beta$-alkyl- or $\beta$-dialkylstyrenes (UV detector No. 655A from Merck, Darmstadt).

(ad) Determination of ethers and tertiary amines still present in the catalyst following the distillative workup.

5 cm$^3$ of catalyst solution, containing from about 1 to 3 mmol of polymerization activity, are titrated under nitrogen with $X$ cm$^3$ of a solution of 1N isopropanol in toluene to a colorless end point.

All of the solvent is then driven over into a receiver cooled with methanol/carbonic acid mixture and the ether content is determined in % by weight by gas chromatography using a GC-3BT gas chromatograph from Shimadzu using a ®Carbowax 20M column at 60° C.

The molar ratio ether/polymerization activity (PA) is obtained from $$\frac{\% \text{ by weight of ether/tertiary amine} \times (5 + X) \text{ cm}^3}{\text{millimoles of } PA \times 7.2} = \frac{\text{millimoles of ether/tertiary amines}}{PA}$$

(b) Characterization of polymers according to the invention (ba) Determination of molecular weight (MW) by GPC The nonfunctionalized samples were used. The GPC instrument used came from Waters. The molecular weights were determined by reference to calibration curves prepared from standardized polymers suitable for calibrating purposes (cf. G. Glöckner, Polymercharakterisierung durch Flüssigkeitschromatographie, Verlag A. Hüthig, Heidelberg, 1982). The measurement was carried out on a 0.25% strength solution in THF at 23° C. and a flow rate of 1.2 cm$^3$/min.

In the case of block copolymers, the MW was taken to be empirically the arithmetic mean between the calibration curves of the two homopolymers corresponding to the composition.

(bb) Determination of the viscosity number

The viscosity number (VN) was determined at 25° C. in toluene (0.5 g of polymer in 100 cm$^3$ of toluene) in accordance with German Standard Specification DIN 51,562.

(bc) Determination of the nitrogen content

The total nitrogen content was determined by the Kjeldahl method.

(bd) Determination of the mechanical properties

The mechanical data (tensile strength at 300% extension, breaking strength and elongation at break) were determined on test specimens blanked in accordance with German Standard Specification DIN 53,455 from 2 mm thick sheets or films press-molded at from 170° to 180° C./60 bar and 150° C./10 bar respectively between Teflon disks.

(be) Crosslinking with diisocyanate 5 g of the polymer were dissolved in 25 g cyclohexane and admixed with 0.33 mmol of a solution of toluylene diisocyanate (TDI) in cyclohexane. After thorough mixing, the solution was cast onto siliconized paper and dried at room temperature.

(bf) Degradation of butadiene/styrene block copolymers
and determination of the molecular weight of polystyrene blocks.

The oxidative degradation of the polybutadiene portion using peroxide/osmium tetroxide is described in detail by Ph. Kubin-Eschger, Angw. Makromol. Chem. 26 (1972), 207, so that no further description is required.

EXAMPLES 1-13

Examples 1-13 describe the preparation of catalysts according to the invention. The reactor used is a 500 cm³ four-neck flask which is fitted with a magnetic stirrer (without Teflon jacket) and a thermometer and which has a rubber cap sealed joint and can be flushed with pure nitrogen. The reactor sits in a coolable waterbath.

The reactor is each time charged with 100 cm³ of a highly purified mixture of 94% by weight of THF and 6% by weight of benzene and about 1.5 g of commercial lithium granules and also 25 mmol of the β-alkylvinylaromatics mentioned in the Table below. The reaction starts at 25° C. depending on the purity of the materials, after from a few minutes to an hour with the contents becoming colored and the temperature rising by 1°-3° C. The reaction ends when internal and bath temperature are in agreement again, in general within from 30 minutes to an hour.

The Table below shows the level of polymerization activity (mmol of PA), the lithium content (mmol), the conversion, the composition of the catalysts and the color thereof.

TABLE

| Example | Alkenyl-aromatic used | Level of PA* mmol | in Lithium mmol | Residual monomer % | HPLC level of Dimer % | Trimer % | Tetramer % | Color |
|---|---|---|---|---|---|---|---|---|
| 1 | A | 13.75 | 14.3 | 5 | 43.3 | Σ51.7 | | orange |
| 2 | B | 24 | 24.7 | 6.8 | 92.5 | — | 0.7 | reddish orange |
| 3 | C | 24.3 | 23 | 9 | 91 | — | — | " |
| 4 | E | 26 | 27.6 | 2.2 | 97.7 | | | " |
| 5 | F | 27 | 25 | 3 | 96.9 | | | " |
| 6 | G | 24.3 | 23.6 | 3.5 | 71 | | 26 | |
| 7 | H | 14.7 | 16 | | no analysis | | | reddish violet |
| 8 | J | 13.1 | 14.0 | | | | | reddish brown |
| 9 | K | 25 | 27 | | | | | reddish orange |
| 10 | L | 25 | 27 | | | | | " |
| 11 | M | 25 | 27 | | | | | " |
| 12 | N | 25 | 26 | | | | | " |
| 13 | O | 24.5 | 25 | | | | | " |

*PA = polymerization activity

In the case of Examples 2 and 4, which were stored at room temperature, the PA was determined after an interval of 10 days. After 100 days it was 24 and 25 mmol respectively, based on starting alkenylaromatic.

EXAMPLE 14

Preparation of a disodium catalyst

The procedure of Examples 1-13 is repeated, except that 3 g of a liquid alloy containing sodium and potassium in a molar ratio of 1:1 are used for dimerization. The alkenylaromatic used is trans-β-hexylstyrene. The reaction has ended after 30 minutes. The dark orangered solution contains 22 mmol of PA and 23.6 mmol of alkali. HPLC reveals 7.5% of starting material and 87.8% of dimer.

EXAMPLES 15 AND 16

These Examples concern the catalytic action of a polycyclic aromatic on the reaction of β-methylstyrene with lithium. The apparatus described in Example 1 is used and in addition the amounts of polycyclic aromatic indicated in the Table below.

| Examples | Phenanthrene mmol | PA mmol | Lithium mmol | Monomer | Dimer | Trimer | Tetramer |
|---|---|---|---|---|---|---|---|
| 15 | 1 | 26 | 28 | — | 95 | — | 5 |
| 16 | 0.25 | 23 | 23 | — | 86.2 | 5.2 | 8.5 |
| Comparison (Example 1) | — | 13.75 | 14.3 | 5 | 43.3 | Σ51.7 | |

EXAMPLES 17–23

These describe the reaction of β,β-dimethylstyrene with lithium in the presence and absence of polycyclic aromatics. Example 1 is repeated, except that in addition the amounts of polycyclic aromatics listed in the Table below are used.

|         | Polycyclic hydrocarbon |                  | Reaction solution |         |                          |       |
|---------|------------------------|------------------|-------------------|---------|--------------------------|-------|
|         |                        |                  | Level in mmol of  |         | Composition (HPLC area %)|       |
| Example | Type                   | Amount in mmol   | PA                | Lithium | Monomer                  | Dimer |
| 17      | —                      | —                | 18                | 23      | 45                       | 54    |
| 18      | Phenanthrene           | 0.25             | 25                | 27      | —                        | 97.4  |
| 19      | "                      | 1.0              | 26                | 28      | —                        | 99.6  |
| 20      | Naphthalene            | 0.25             | 22                | 25.5    | —                        | 99.5  |
| 21      | Phenanthrene           | 0.25             | 22                | 26.5    | —                        | 99.2  |
| 22      | Biphenyl               | 0.5              | 20                | 23      | —                        | 96.2  |
| 23      | "                      | 2.5              | 24                | 25      | —                        | 98.4  |

In the case of phenanthrene, particularly small amounts, for example 1 mol %, based on starting β,β-dimethylstyrene, are sufficient to ensure complete conversion to the dimer. An unexpected result is the high polymerization activity of Comparative Example No. 17. The properties of the catalyst prepared without polycyclic aromatics, however, are not optimal, giving high proportions of monofunctionally grown polymers in polymerization trials (see Example 33), as is evident from their mechanical properties and polymer analysis.

EXAMPLE 24

Preparation of a low-ether catalyst with tetrahydrofuran (THF).

The reactor of Example 1 is charged with 80 cm³ of THF, 20 cm³ of benzene and 3 g of lithium. 28.2 g=150 mmol of β-hexylstyrene are added to this mixture. The reaction starts immediately with coloring and warming. Cooling is applied to prevent the temperature from rising above 28° C. After 30 minutes the reaction has ended. Analysis indicates a PA content of 147 mmol and a lithium content of 150 mmol.

141 mmol of the catalyst are transferred with a syringe to a 500 cm³ distillation flask which is ventilated with pure nitrogen and which has previously been rinsed out beforehand with an active catalyst solution of low concentration, to remove impurities. THF is drawn off in the waterbath at 25° C. under reduced pressure and stirring by magnet until the solution becomes viscous. 20 cm³ of a 1:1 mixture of benzene/cyclohexane which has previously been titrated with the same catalyst to a slight orange color are then added, and the mixture is again evaporated under reduced pressure until the solution becomes viscous. The residue is taken up with the same solvent mixture, transferred completely with a syringe by washing into a stock reservoir vessel under pure nitrogen and made up to 100 cm³, and the PA content is determined.

PA: 141 mmol. A 2 cm³=2.8 mmol sample was taken of the solution, titrated with 0.1N isopropanol/toluene solution until colorless and, as described, analyzed for THF by gas chromatography. A THF content of 0.21 g corresponding to 2.92 mmol is found. The THF/PA ratio is thus 1.04.

EXAMPLE 25

Preparation of a low-ether catalyst with tetrahydrofuran

The reactor of Example 1 is charged with 40 cm³ of THF, 2.6 cm³ of anisole (27 mmol), 3 g of lithium granules and 4 g of β-butylstyrene (25 mmol). The reaction starts immediately, and heat is evolved. After 60 minutes the PA content is 26.5 mmol and the lithium content 24.5 mmol.

The reactor contents are transferred with a syringe and by rinsing with cyclohexane into the distillation flask of Example 24, and 8 cm³ of t-butylbenzene are added. While stirring with an uncoated iron magnet the low-boiling solvents are distilled off in a water bath at 25° C. under decreasing pressure into a methanol/carbon dioxide cooled receiver until a pressure of 0.5 mbar is reached and the temperature in the flask has again risen to 23° C. The catalyst precipitates toward the end of the operation in the form of a finely divided pale orange suspension. By means of a syringe and by washing with a cyclohexane/benzene mixture all of it is transferred into a stock reservoir vessel under pure nitrogen and made up to 50 cm³.

Level of polymerization activity: 25 mmol (calculated against starting amount of β-butylstyrene).

Ratio of THF/PA=1.01.

EXAMPLE 26

Preparation of a low-ether catalyst with diethyl ether.

The reactor of Example 1 is charged with 15 cm³ of diethyl ether, 3 g of lithium granules, 10 cm³ of cyclohexane, 16 cm³ of 2-butylbenzene and 10.75 g (50 mmol) of trans-1-phenyl-3-ethyl-1-octene. The reaction, which starts immediately, takes 30 minutes with cooling at from 25° to 28° C. A PA content of 48.8 mmol and a lithium content of 45.5 mmol are measured.

The reactor contents are transferred by rinsing with 10 cm³ of cyclohexane into the distillation flask of Example 24 and distilled with stirring with a magnet in a waterbath at 25° C. under decreasing pressure until a pressure of 0.5 mbar has been reached, the temperature at the base of the column has risen again to 23° C. and the solution becomes viscous. After atmospheric pressure has been restored, the solution is diluted with 20 cm³ of cyclohexane and transferred completely with a syringe by washing with cyclohexane into a stock reservoir vessel under nitrogen and made up to 50 cm³.

PA: 46 mmol. Ratio diethyl ether/PA=0.123.

EXAMPLE 27

Preparation of a low-ether catalyst with diisopropyl ether.

Example 26 is repeated, except that the t-butylbenzene is replaced by n-octane and the diethyl ether by diisopropyl ether.

A PA content of 49 mmol, a lithium content of 50.7 mmol and an ether/PA ratio of 0.112 molar are found.

EXAMPLE 28

Preparation of a low-ether catalyst with dimethyl ether

The reactor of Example 1 is charged with 50 cm$^3$ of methylcyclohexane and 5.375 g (25 mmol) of trans-1-phenyl-3-ethyl-1-octene, and purified dimethyl ether gas is passed over the liquids being mixed with a magnetic stirrer. The reaction starts after 5 minutes, the temperature rising from 21.5° to 23.5°, and has ended after one hour. The PA content is 25.2 mmol and the lithium content 24.4 mmol. The reactor contents are transferred by rinsing with 10 cm$^3$ of methylcyclohexane into the distillation flask of Example 24, and 40 cm$^3$ of the flask contents are distilled off with stirring at internal temperatures of around 0° C. and under finally 10 mm Hg. After atmospheric pressure has been restored, the solution is diluted with 15 cm$^3$ of methylcyclohexane, transferred with rinsing into a stock reservoir vessel under pure nitrogen and made up to 60 cm$^3$.

PA (based on starting amount): 25.5 mmol, lithium content 24.7 mmol.

Molar ratio DMA/PA=0.087.

EXAMPLE 29

Preparation of a catalyst in the presence of triethylamine

The reactor of Example 1 is charged with 35 cm$^3$ of methylcyclohexane, 15 cm$^3$ of triethylamine, 3 g of lithium granules and 25 mmol of trans-1-phenyl-3-ethyl-1-octene. The reaction starts after 5 minutes and has ended after 45 minutes. The reactor then contains 25.2 mmol of PA and 24.5 mmol of lithium. Polymerization trials

EXAMPLES 30-38

The polymerization trials are carried out in a reactor comprising a 10-1 glass flask equipped with a stirrer, a reflux condenser operated with brine at −30° C., a calibrated dropping funnel likewise equipped with a brine reflux condenser, a rubber cap sealed joint, pure nitrogen inlet and outlet means and a heating or cooling jacket. The nitrogen is freed of traces of moisture and oxygen by washing with a white oil containing 2% by weight of lithium butyl. The reactor is initially boiled out with a solution of lithium butyl in cyclohexane containing a little styrene. The orange color which serves to indicate the activity of the solution must be present right to the end. The solution is withdrawn, and the kettle is charged with 3 l of cyclohexane previously purified by passage through a molecular sieve column. The impurities still present are titrated away at 40° C. with the catalyst solution according to the invention being introduced by means of a calibrated syringe through the rubber cap until a slight orange color persists.

Examples 30-38 below concern the preparation of 3-block copolymers S-B-S of the composition 27% by weight of styrene and 73% by weight of butadiene with a target molecular weight of 60,000. To this end the reactor is charged after the titration with 10 mmol each time of the catalysts named in the Table below and then with 50 mm$^3$ (31.3 g) of butadiene and heated to 45° C., and the remaining butadiene (amounting in total to 300 cm$^3$ or 187.5 g) is added while the temperature rises to 70° C. After the butadiene has been added, a temperature of 60° C. is maintained for one hour, a sample is taken and 89 cm$^3$ (81 g) of styrene are added.

After 60 minutes the mixture is cooled down to 40° C., a further sample is taken, and 11 mmol of propylenediaziridine are added. The viscosity rises with gel structure formation. After about one hour 1 cm$^3$ of ethanol is added to discontinue the polymerization, and the fluent solution is precipitated by pouring into 5 l of ethanol containing 0.5% by weight of di-t-butyl-pcresol. Following repeated kneading with alcohol the polymer is dried at 60° C. overnight in a vacuum drying cabinet.

The following Tables show the analytical measurements and the mechanical properties:

| | | | | Polymerization of 3-block styrene-butadiene-styrene copolymers: analytical data | | | | | | | |
|---|---|---|---|---|---|---|---|---|---|---|---|
| | | | | | | | Degradation by osmium tetroxide Polystyrene blocks | | Nitrogen content | | |
| No. | Catalyst of Example | THF Ratio PA:THF | % by weight in solution | GPC PB MW | PB + PS MW | VN | obs./calc.* | total % of PS & VN | % by weight | % by weight calc.** | Polymer properties |
| 30 | 1 | 7.4 | 0.22 | 43000 | 60000 | 71.3 | 9000/8100 | 25.3 | 9.1 | 0.079 | 0.093 | tough |
| 31 | 2 | 45 | 1.37 | 52000 | 70000 | 80.8 | 10000/9450 | 29 | 11.9 | 0.089 | 0.080 | " |
| 32 | 3 | 22 | 0.67 | 53000 | 70000 | 97.6 | 7000/9450 | 29.6 | 12.5 | 0.075 | 0.080 | " |
| 33 | 4 | 22.3 | 0.69 | 45000 | 60000 | 78.1 | 9000/8100 | 28.6 | 10.1 | 0.10 | 0.093 | " |
| 34 | 24 | 1 | 0.03 | 50000 | 80000 | 105.8 | 6500/10800 | 24.3 | 10.8 | 0.074 | 0.070 | " |
| 35 | 8 | | | 50000 | 70000 | 81 | — | — | — | 0.085 | 0.080 | " |
| 36 | 6 | 22 | 0.67 | 75000/ 50000*** | 110000/ 70000*** | 79 | 6500 | 29.5 | 11.7 | 0.088 | 0.08 | " |
| 37 | 17 | 45 | 1.37 | 35000 | 43000 | 66.8 | 10000/5800 | 26.2 | 11.0 | 0.080 | 0.13 | plastic |
| 38 | 19 | 44 | 1.34 | 38000 | 50000 | 63.8 | 9000/6750 | 26.5 | 11.0 | 0.078 | 0.11 | tough |

*The molecular weight of the polystyrene blocks is calculated for the GPC-determined molecular weight of starting polymers on the assumption that both chain ends consist of polystyrene blocks.
**The theoretical nitrogen content is determined on the assumption that each chain end carries 2 amino groups.
***2 polymer peaks

| No. | Catalyst of Example | Mechanical properties and configuration | | | Butadiene configuration FTIR | | |
|---|---|---|---|---|---|---|---|
| | | Tensile strength at 300% extension N/mm² | Breaking strength N/mm² | Elongation at break % | % 1,4-trans | % 1,2- | % 1,4-cis |
| 30 | 1 | 2.54 | 5.91 | 771 | 27.4 | 54.1 | 18.5 |
| 31 | 2 | 2.03 | 11.59 | 813 | 25.5 | 57.1 | 17.4 |
| 32 | 3 | 2.65 | 11.65 | 879 | 32.5 | 46.2 | 21.3 |
| 33 | 4 | 2.23 | 7.65 | 751 | 32.3 | 48.0 | 19.6 |
| 34 | 4 | 2.29 | 4.95 | 784 | 46.2 | 27.5 | 26.4 |
| 35 | 6 | 3.99 | 11.54 | 882 | 31.6 | 49.0 | 19.4 |
| 36 | | | | | | | |
| 37 | 17 | | not measurable | | 25.1 | 57.3 | 17.6 |
| 38 | 19 | 1.88 | 4.05 | 815 | 26.0 | 56.8 | 17.2 |
| | Comparative run | 1.95 | 9.62 | 577 | 57.4 | 12.2 | 30.4 |

***The SBS-3-block copolymer, 27% by weight of styrene, 73% by weight of butadiene and MW 68,000 is prepared with Lithium butyl by successive polymerization of styrene→butadiene→styrene in cyclohexane at 70° C. in a conventional manner. All the polymers, with the exception of the polymer from the comparative run, if admixed in solution in cyclohexane with toluylene diisocyanate, cast and dried, give elastic, insoluble films. FTIR = Fourier transform infrared spectroscopy The Examples permit the following statements:
1. The catalyst according to the invention, except Example 37, give the desired and/or theoretically predicted MWs within the variation due to different MW distributions.
2. From the nitrogen levels of the polymers and the MWs of the polystyrene blocks obtained therefrom by osmium tetroxide degradation it follows that, with the exception of Example 37, three-block copolymers are present. These statements are confirmed by the mechanical properties, which are similar to those of the comparative test.
3. In Example 37 there are present appreciable or predominant portions of two-block copolymer.
4. By polymerization in the presence of very low amounts of THF (Example 34) the polybutadiene block as expected contains smaller proportions of 1,2-configuration.

EXAMPLES 39–44

A 500 cm³ flask equipped with a magnetic stirrer, a waterbath, a thermometer and pure nitrogen inlet and outlet means is charged each time with 100 cm³ of purified toluene and 10 cm³ of styrene. The initial charge is titrated to a pale orange color with the catalyst to be used, which is injected with a syringe through a rubber membrane and is immediately admixed with an amount of catalyst solution corresponding to 0.5 mmol of polymerization activity. The mixture is polymerized at 50° C. for one hour, cooled at 40° C. and reacted with 0.6 mmol of propylenediaziridine. After 40 minutes the polystyrene is precipitated by pouring into ethanol, washed on the suction filter with alcohol and dried. The polymers are found to have the following values:

| No. | Catalyst of Example | MW calc. | MW GPC | N content in % (Kjeldahl) observed | N content in % (Kjeldahl) caculated |
|---|---|---|---|---|---|
| 39 | 1 | 40000 | 57000 | 0.094 | 0.098 |
| 40 | 5 | " | 47000 | 0.13 | 0.12 |
| 41 | 5 | " | 48000 | 0.12 | 0.12 |
| 42 | 18 | " | 60000 | 0.089 | 0.093 |
| 43 | 14 | " | 75000 | 0.012 | 0.075 |
| 44 | 29 | " | 48000 | 0.11 | 0.12 |

In Example 43 the bifunctional sodium catalyst of Example 14 is used. The result is a polystyrene having a broad molecular weight distribution. The functionalization is only possible in poor yield.

EXAMPLE 45

Preparation of a functionalized polybutadiene oil.

In the apparatus of Example 1, 3,000 cm³ of cyclohexane are titrated with the catalyst of Example 24 to a pale orange color and then admixed with an amount of catalyst of Example 24 corresponding to 100 mmol of PA. 50 mm³ of butadiene are then added, the mixture is heated to 60° C., and at that temperature a further 350 cm³ (together with 250 g) of butadiene are added at such a rate as to just avoid refluxing. After all the butadiene has been added, the mixture is maintained at 60° C. for a further 30 minutes, and then cooled down to 40° C. and functionalized with 220 mmol of propylenediaziridine, and the solution begins to show a gel-like viscosity. After 30 minutes of stirring the reactor contents are precipitated with 5 l of methanol. The polybutadiene oil which settles out is stirred up 3 times with 1 l of methanol each time, mixed with 0.5 g of di-t-butyl-p-cresol and dried at 60° C. under reduced pressure. The result is a pourable polybutadiene oil of MW 5,500 (GPC) and narrow MW distribution. The Kjeldahl nitrogen content is 0.95% (theory: 1.02%). FTIR analysis indicates a configuration of 41.1% of 1,2-, 23.4% of 1,4-cis and 35.5% of 1,4-trans structure for the incorporated polybutadiene.

4 mmol of hexamethylene diisocyanate (0.672 g) are stirred rapidly with a glass rod at room temperature into 5 g of the oil in a penicillin glass and the mixture is poured onto siliconized paper. The mixture solidifies within minutes to a colorless, elastic rubber.

EXAMPLE 46

Preparation of a functionalized polybutadiene oil.

Example 45 is repeated, except that 15 mmol of the catalyst of Example 25 are used and 150 g of butadiene are polymerized. The polymer has an MW of 11,000 and a narrow MW distribution. The Kjeldahl nitrogen content is 0.55% (calculated 0.52%). The incorporated polybutadiene is 39% in 1,2-, 24% in cis-1,4- and 37% in trans-1,4-configuration.

We claim:
1. A process for preparing a bifunctional initiator for polymerizing an anionically polymerizable monomer, which comprises dimerizing an alkenylaromatic compound of the general formula I

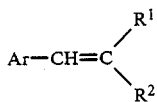
(I)

where Ar is pyridy, quinolyl or aromatic hydrocarbyl which may be substituted by alkyl or another group inert toward organoalkali metal compounds, $R^1$ is linear or branched alkyl, cycloalkyl, alkenyl or aralkyl where at least the carbon adjacent to the double bond is saturated and aliphatic, $R^2$ is hydrogen or linear or branched alkyl, cycloalkyl, alkenyl or aralkyl where at least the carbon adjacent to the double bond is saturated and aliphatic, and where $R^1$ and $R^2$ may be part of a common cycloaliphatic ring, in the presence of one or more ethers and of one or more tertiary amines and in the presence or absence of an inert aliphatic, alicyclic or aromatic solvent, at from $-20°$ to $+70°$ C. with an alkali metal under an inert gas atmosphere.

2. A process as claimed in claim 1, wherein Ar is phenyl, $R^1$ is linear, branched or alicyclic alkyl of from 5 to 10 carbon atoms and $R^2$ is hydrogen, the alkali metal is lithium, from 1 to 3 moles of an aliphatic linear and/or branched ether or tertiary amine of from 2 to 8 carbon atoms are used per mole of I and this ether or amine is removed after the reaction in the presence of a high-boiling aliphatic or alicyclic solvent by distillation at below 25° C. down to a residual level of from 5 moles to 0.1 mole per mole of polymerization-active lithium.

3. A process as claimed in claim 1, wherein a polycyclic aromatic hydrocarbon which catalytically promotes the dimerization is present in an amount of from 0.001 to 50 mol %, based on the alkenylaromatic.

4. A process as claimed in claim 3, wherein from 1 to 20 mol % of the polycyclic aromatic compound are present.

5. A process as claimed in claim 3, wherein Ar is phenyl, $R^1$ and $R^2$ are each linear or branched alkyl of from 1 to 10 carbon atoms or together form a constituent of a cycloaliphatic ring of from 5 to 12 carbon atoms, the polycyclic hydrocarbon used is phenanthrene and the alkali metal used is lithium.

6. A process as claimed in claim 1, wherein the ethers and/or tertiary amines used for preparing the dilithium compound according to the invention are partially or completely removed after the reaction.

* * * * *